(12) United States Patent
Hansen et al.

(10) Patent No.: US 6,902,551 B2
(45) Date of Patent: Jun. 7, 2005

(54) OSTOMY APPLIANCE WITH BARRIER MEMBER HAVING A SINGLE COUPLING RING WITH TWO COUPLING AREAS FOR CONNECTION OF INNER AND OUTER BAG MEMBERS

(75) Inventors: Soeren Hansen, Helsingeer (DK); Birthe Vestbo Andersen, Espergaerde (DK)

(73) Assignee: Coloplast A/S, Humlebaek (DK)

( * ) Notice: Subject to any disclaimer, the term of this patent is extended or adjusted under 35 U.S.C. 154(b) by 37 days.

(21) Appl. No.: 10/257,987

(22) PCT Filed: May 3, 2001

(86) PCT No.: PCT/DK01/00308
§ 371 (c)(1),
(2), (4) Date: Oct. 30, 2002

(87) PCT Pub. No.: WO01/82846
PCT Pub. Date: Nov. 8, 2001

(65) Prior Publication Data
US 2003/0153883 A1 Aug. 14, 2003

(30) Foreign Application Priority Data
May 3, 2000 (DK) .................................. PA 2000 00732

(51) Int. Cl.[7] .................................................. A61F 5/44
(52) U.S. Cl. ...................................... 604/342; 604/277
(58) Field of Search ................................ 604/277, 327, 604/332, 337–339, 341, 342, 344

(56) References Cited

U.S. PATENT DOCUMENTS

| | | | |
|---|---|---|---|
| 5,209,744 A | 5/1993 | Abe et al. | 604/342 |
| 5,423,782 A | 6/1995 | Wolrich | 604/339 |
| 5,591,144 A | * 1/1997 | Smith et al. | 604/327 |
| 5,690,623 A | * 11/1997 | Lenz et al. | 604/333 |
| 5,785,695 A | 7/1998 | Sato et al. | 604/339 |
| 6,312,415 B1 | * 11/2001 | Nielsen et al. | 604/342 |

FOREIGN PATENT DOCUMENTS

| | | |
|---|---|---|
| DE | 195 19 069 | 11/1996 |
| EP | 0 703 762 | 4/1996 |
| EP | 0 768 848 | 4/1997 |
| EP | 0 821 925 | 2/1998 |
| GB | 2 265 832 | 10/1993 |
| GB | 2 306 889 | 5/1997 |
| WO | 94/18919 | 9/1994 |

* cited by examiner

*Primary Examiner*—Larry I. Schwartz
*Assistant Examiner*—Michael G. Bogart
(74) *Attorney, Agent, or Firm*—Jacobson Holman PLLC

(57) ABSTRACT

An ostomy appliance including an adhesive barrier member having a hole for receiving a stoma, ureter, or catheter, an outer receiving member or bag releasably attached to the adhesive barrier member, and a disposable inner bag liner releasably attached to the adhesive barrier member. A single base coupling ring is attached to the barrier member and includes a first coupling area on an inner surface thereof, relative to the hole, and a second coupling on an outer surface thereof. The inner bag, which is coupled to the barrier member using an inner bag coupling ring, is coupled to the barrier member at the first coupling area and the outer receiving member is coupled to the barrier member at the second coupling area, such that both the inner bag and outer receiving member are mounted on the same single barrier member ring.

16 Claims, 3 Drawing Sheets

Flat

Round

OSTOMY APPLIANCE WITH BARRIER MEMBER HAVING A SINGLE COUPLING RING WITH TWO COUPLING AREAS FOR CONNECTION OF INNER AND OUTER BAG MEMBERS

This is a nationalization of PCT/DKQ1/00308, filed May 3, 2001 and published in English.

BACKGROUND OF THE INVENTION

1. Field of the Invention

The present invention relates to an ostomy appliance comprising a body side member, a receiving bag and a disposable bag liner; and a disposable bag liner for use together with an ostomy appliance.

In connection with surgery for a number of diseases in the gastrointestinal or urinary tract a consequence is, in many cases, that the colon, the ileum or the ureter has been exposed surgically and the patient is left with an abdominal stoma, or, in nephrostomy or ureterostomy, the ureter or a catheter is exposed in the back or the chest region or abdominal region, and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma/ureter/catheter. Also in connection with a fistula, the patient will have to rely on an appliance to collect the bodily material emerging from such opening.

Ostomy appliances are well known. Such appliances may be two-piece or one-piece appliances. In both types of appliances, an adhesive barrier member (or base plate) is attached to the wearer's abdomen/back/chest. In case of a one-piece appliance, a receiving member or bag is attached to the base plate. In case of a two-piece appliance, the adhesive barrier member forms part of a body side member and a receiving member or bag is attached releasably to the body side ostomy member for receiving exudates from the stoma.

When using one-piece appliances, the whole appliance, including the adhesive skin barrier securing the appliance to the skin is normally removed and replaced by a fresh appliance. When using two-piece appliances, the body side ostomy ember is left in place up to several days, and only the receiving member or bag attached to the body side member is replaced. The attachment means for attaching an ostomy receiving bag may be a system known per se comprising matching coupling rings or matching flanges and adhesive surfaces engaging with and sealing against a flange area of the body side member.

The service time of the body side ostomy member depends on the amount and aggressiveness of the exudates and of the tightness of the sealing between the ostomy and the body side ostomy member.

A known major problem with such receiving bags is that it can be difficult to dispose of the used bag in a convenient and hygienic manner. Some ostomists will cut the used bags open, e.g. by cutting off an edge thereof and depositing the contents into a WC for flushing away and disposing or depositing the empty bag in a waste bin. Such disposal of used bags and the contents therein is indeed unhygienic and unpleasant for the user, and in view of this a number of proposals have been made for ostomy bags which may be flushed down a WC.

2. Description of the Related Art

Thus, U.S. Pat. No. 5,423,782 (Wolrich) discloses a disposable ostomy bag liner apparatus including a unitary flexible bag having a main body portion, a tapered portion and a flange portion in which the tapered portion is disposed adjacent the main body portion and together, the main body portion and tapered portion define an interior portion of the bag for receiving and hold intestinal waste material. The patent discloses a bag liner for use by colostomy and some ileostomy patients which is easy to install in a conventional ostomy bag, which has provisions to allow for escape of gas admitted into the liner and which is relatively inexpensive to produce.

EP Patent No. 0 768 848 (Welland Medical Limited) discloses a biodegradable, flushable ostomy bag liner comprising inner walls formed from polyvinylacetate/polyvinylalcohol film of a grade which disintegrates within 60 seconds in water at 50° C. but retains its structural integrity in water at 25° C. for at least two days, outer walls formed from a non-woven fabric which disintegrates in water at 25° C., means defining an opening in the inner and outer walls for receiving bodily waste from the stoma patient, an adhesive flange being secured to at least an inner wall of the liner and surrounding the said opening, wherein the walls of the inner and outer bags are unconnected and form a non-laminar arrangement over the greater part of their area, but are connected around their peripheral margins and in the region of the adhesive flange.

EP Patent No. 0 703 762 (Welland Medical Limited) forms basis for the invention disclosed in EP Patent No. 0 768 848 above and discloses a drainage bag for receiving bodily waste, the drainage bag containing an outer bag, a water-impermeable inner bag enclosed within the outer bag, the inner bag being of a structure which is weakened upon immersion in a WC bowl such that it becomes limp and is less buoyant thereby enabling it to be flushed away easily, and means defining an orifice to enable bodily waste to be received by the inner bag in which the outer bag is water-impermeable and is formed from a material which acts as a barrier to flatus gases. The outer bag is provided with a flatus filter, the inner bag is permeable to flatus gases, and the outer and inner bags are detachably secured together in the region of the orifice.

GB Patent Application No. 2 306 889 (Alcare Co Ltd) discloses a body waste receiving appliance comprising an adhesive plate with an opening to a wastes discharge hole or opening formed on the surface of a human body, a first flange secured to the non-adhesive side of said adhesive plate and having an opening corresponding to the opening of said adhesive plate, a second flange detachably mounted at the opposite side, with reference to said adhesive plate, of said first flange and having an opening corresponding to the opening of said first flange and having an opening corresponding to the opening of said first flange, an outer pouch secured at the opposite side, with reference to the adhesive plate, of said second flange and having an opening corresponding to the respective openings of said adhesive plate, said first flange and said second flange, and an inner pouch for receiving the body wastes through the respective openings of said adhesive plate and said first flange, said inner pouch being housed inside the outer pouch in such a manner as to be separable therefrom, said outer pouch being formed of a non-water-soluble film, while said inner pouch being formed of a water-soluble film which is dissolved or disintegrated in water, said inner pouch being replaceable.

GB Patent Application No. 2 265 832 (Bettison) discloses an ostomy bag with an inner dividing means in the form of an open, inner bag communicating with the internal space of the outer bag having the overall effect of dividing the interior of the bag into an inlet section and an outlet section communicating in the vicinity of the bottom of the bag.

EP Patent Application No. 0 821 925 (Quacquarella) discloses an ostomy appliance comprising a reusable outer bag and a disposable inner bag, means for securing the two bags together and to the stoma, means for inserting and removing the inner bag from the outer bag, and means for closing the outer bag once the inner bag is in place.

The purpose of the present invention is to provide an ostomy appliance combining the advantages of using separate, flushable inner bags with a safe, hygienic and discreet management of the collected waste with maximum safety against soiling parts of the appliance not to be substituted when changing the inner bag. Non of the above-referenced patents disclose an ostomy bag comprising a disposable inner bag which stays with full engagement with the coupling area of a body side member after detaching the outer bag.

SUMMARY OF THE INVENTION

The present invention relates to an ostomy appliance comprising a body side member, a receiving bag and a disposal bag liner.

The present invention furthermore relates to a disposable bag liner for use together with an ostomy appliance.

BRIEF DESCRIPTION OF THE DRAWINGS

The invention is disclosed more in detail with reference to the drawings in which.

DETAILED DESCRIPTION OF THE PRESENT INVENTION

Figure 1:
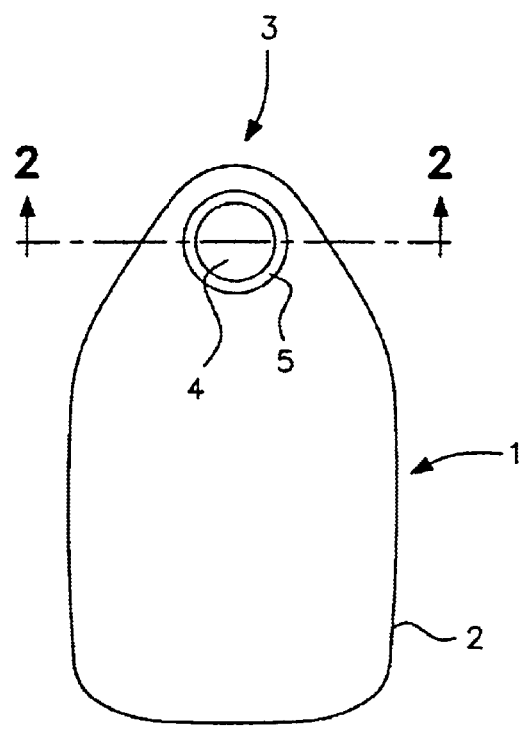
FIG. 1 shows an embodiment of an ostomy appliance inner bag of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention relates to an ostomy appliance comprising an adhesive barrier member (or base plate), said barrier member having a hole for receiving a stoma, ureter, or catheter and barrier wafer to be attached to the wearer's abdomen, back or chest; an outer receiving member or bag releasably attached to the adhesive barrier member, said bag having a hole for receiving wastes exiting the stoma, ureter or catheter; and a disposable inner bag liner releasably attached to the adhesive barrier member wherein the disposable inner bag liner having a hole for receiving wastes exiting the stoma, ureter or catheter is attached releasably to the adhesive barrier member in a first coupling area by first coupling means and the outer receiving member is attached releasably to the adhesive barrier member by second coupling means, in which the first and second coupling areas are in the form of one or more coupling rings and the first and second coupling means are in the form of matching coupling rings and wherein the outer diameter of the first coupling means is smaller than the inner diameter of the second coupling means.

The present invention fulfils the purpose of the invention as stated above in that the coupling rings for attaching the inner bag liner are placed in such a relationship to each other that the outer receiving member may be detached separately leaving the inner bag liner, which is closed apart from the hole for receiving wastes, in full engagement with the first coupling area and thus, a barrier is provided against contact between the wastes exiting from the stoma and the coupling system for the outer receiving member and provides an extra safety against contact between the wastes exiting from the stoma and the skin and guide the waste into the bag liner.

Furthermore, the present invention will not jeopardise the option of using a convex element known per se for e.g. retracted stomas.

The use of a coupling ring furthermore gives a better safety against trapping of air in the inner bag liner when disposing the same in the WC bowl for flushing as the opening of the bag is kept open.

The shape of the inner bag liner is preferably in the form of a bag which is narrower at the open inlet end and wider in the closed end which maximises the capacity of the bag and minimises the risk of trapping air which might hamper the disposal by flushing.

An adhesive barrier member (or base plate) and an outer receiving member or bag for use in an ostomy appliance according to the invention may be made from materials conventionally used for the preparation of ostomy appliances in a manner known per se in the field.

Coupling rings for use in the present invention may be any conventional coupling rings for coupling adhesive barrier member (or base plate) and receiving bags such as the coupling rings disclosed in WO94/18919

In one embodiment of the invention, the ring is flexible in a direction perpendicular to the plane of the ring and relatively stiff in radial direction rendering the detachment of the bag more easy. This may e.g. be obtained by providing the ring with weakening zones known per se being weaker in non-radial direction.

At least the outer edge of the ring may suitably be of a relatively soft material providing friction sealing enhancing the safety against leak.

In another embodiment of the invention, the ring is made from a material being biodegradable.

The ring may be sealed to the inner bag liner or, in a further embodiment of the invention the ring is a separate ring which may be used several times. In this embodiment, the open end of the inner bag liner is preferably elaborated in a manner enabling a locking of the bag by passing the open end of the bag through the ring and folding the end of the bag back outside of the ring so that the ring is enclosed in the folded part of the bag and the bag is locked when engaging the ring with the coupling ring of the base plate. When disposing the used bag, the bag is detached and its surface having been in contact with the waste exiting the stoma is kept from contact with the coupling parts ensuring a high degree of safety against soiling the coupling ring, the base plate, or the hands of the user.

In the alternative, the ring is placed inside the open or free end of the bag liner and the open or free end of the bag is folded inside the ring so that the ring is enclosed in the folded part of the bag and the bag is locked when engaging the ring with the coupling ring of the base plate.

In this embodiment, the open or free end of the bag liner will stretch into the bag and form a sealing against the side of the stoma. It is preferred that the outer rim of the open end of the bag liner is provided with a layer of adhesive which may form a direct sealing against the stoma and reduce the risk of soiling the coupling area of the base plate which is intended to stay on the skin for a longer period of time than the individual receiving bags. In this embodiment it may be preferred to use the separate coupling ring as a disposable ring. In this embodiment it is preferred that the bag is wider in the closed end for facilitating the emptying of the bag from air when dumped in the WC bowl for flushing.

In one embodiment of the invention, the first and second coupling means are in the form of concentric coupling rings.

In another, preferred embodiment of the invention, the first and second coupling areas are located on one coupling ring for coupling a receiving member to the adhesive barrier member wherein the first coupling surface is located at the inner surface of the coupling ring and the second coupling surface is located at the outer surface of the coupling ring. This embodiment will provide extra safety against leak or unintended detachment when using a locking ring as disclosed in WO 94/18919 also locking the ring of the inner bag liner.

It is preferred that the first coupling surface is in the form of a groove in the inner surface of the coupling ring as this provides a reliable safety against leak and also clearly indicates when the coupling means of inner bag liner engages properly with the coupling ring. This renders the use more safe as it is often difficult to obtain a good view of the area of the stoma where the bag is to be attached for ensuring a proper placement without having access to a mirror.

In another preferred embodiment, the first coupling surface is in the form of a recess at the proximal side or beneath the coupling ring of the base plate giving the same advantages as stated above. For this embodiment it is preferred that the coupling surface of the ring of the inner bag liner is located on an outwardly extending rib.

The inner bag liner may be made from a material being essentially water-soluble with the proviso that it is not dissolved until disposal thereof. Such material may e.g. be of the kind mentioned in EP Patent No. 0 768 848.

The inner bag liner is preferably made from a material not being gas tight and thus permitting intestinal gasses entering the bag to diffuse through the inner bag liner without giving rise to ballooning for management by a conventional gas venting and filtering system placed on the outer bag. The inner bag liner is preferably impermeable to water and water vapour in order to avoid leaking of liquid or passing of water vapour which would start a deterioration of the outer layer of the bag liner.

Thus, the inner bag liner is suitably made from a thin, water-impermeable sheet, which is not gas-tight. The bag liner is suitably in the form of a coextruded or laminated sheet having a layer of water soluble material such as PVA, PVAL or EVAL at the outer surface. The inner surface may suitably be made from a material which may be processed into a thin layer without pin holes such as PE, EVA, PVC, PP, or a polyester which layer is impermeable for water vapour. The outer material may e.g. be in the form of a sheet or a non-woven material.

In a second aspect, the invention relates to a disposable inner bag liner for receiving effluents or waste products of the body for use together with an ostomy appliance comprising an adhesive, flexible skin barrier member for securing the appliance to the user's skin said barrier member having a hole for receiving a stoma, ureter or catheter and barrier wafer to be attached to the wearer's abdomen back or chest; and a collection bag having a hole for receiving wastes exiting the stoma, ureter or catheter, wherein the disposable inner bag liner has a hole for receiving wastes exiting the stoma, ureter or catheter and is releasably attachable to the adhesive barrier member in a first coupling area by first coupling means and the collection bag is releasably attachable to the adhesive barrier by second coupling means, in which the first and second coupling areas are in the form of one or more coupling rings and the first and second coupling means are in the form of matching coupling rings and wherein the outer diameter of the first coupling means is smaller than the inner diameter of the second coupling means.

In a preferred embodiment of the disposable inner bag liner, the first coupling means is in the form of a coupling ring for engaging with a first coupling area located at the inner surface of a coupling ring for coupling a collection bag to the adhesive barrier member.

In a further, preferred embodiment of the dispersible inner bag liner of the invention, the first coupling means is in the form of an exchangeable inner bag coupling ring not being attached to the bag liner.

In a further, preferred embodiment, the exchangeable coupling ring has an inner diameter $d_1$ and an outer diameter $d_2$ and the flattened inner bag has an open end having a width W and the inner bag liner in an open state having an essentially circular opening has a diameter D1 wherein the relation D1<d2 is fulfilled.

Still further, in a preferred embodiment, the open end with W of the inner bag liner and the coupling ring outer diameter $d_2$ fulfils the relation W>$d_2$

DESCRIPTION OF THE PREFERRED EMBODIMENTS

The invention is now explained more in detail with reference to the drawings showing preferred embodiments of the invention.

In FIG. 1 is shown an embodiment of an inner bag liner of the invention in the form of a bag generally designated by 1. The bag 2 is made from a thin, water-impermeable sheet, which is preferably not gas-tight. This allows air to pass through the inner bag liner to let out through a conventional ostomy filter system for managing gas, and no special precautions has to be taken in order to prevent ballooning. The inner bag liner preferably has a general trapezoid shape being narrower in the upper inlet end 3. In this embodiment, the inlet is in the form of an opening 4 at the side of the bag, near the top. The bag has an inner bag coupling ring 5 secured to the bag which may engage with a corresponding coupling ring situated on a barrier member or base plate (see FIG. 2).

Figure 2:
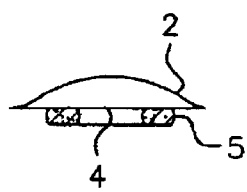
FIG. 2 shows a section of the embodiment of FIG. 1 along the line 2—2.

FIG. 2 shows a sectional view of the inner bag shown in FIG. 1 along the line 2—2. The inner bag coupling ring 5 is situated at the outer side of the bag 2 surrounding the inlet opening 4.

Figure 3:
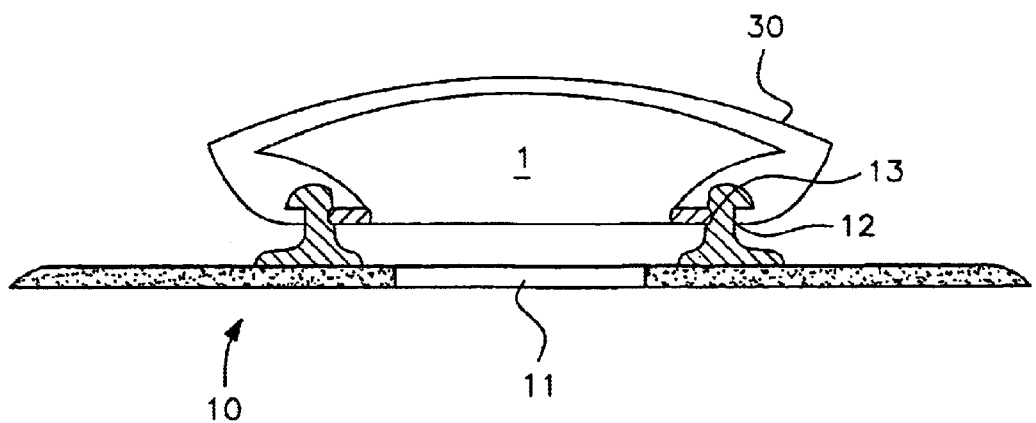
FIG. 3 shows the embodiment of an inner bag shown in FIG. 1 when placed in mesh with a coupling ring attached to a base plate.

FIG. 3 shows a sectional view of a base plate generally designated 10 having a hole 11 for accommodating a stoma and a coupling ring 12 for attaching a conventional collecting bag and showing the embodiment of an inner bag 1 shown in FIGS. 1 and 2 when placed with the inner bag coupling ring 5 in mesh with a groove 13 at the inner side of coupling ring 12 of the base plate. As will be appreciated, a conventional outer receiving member or collecting bag 30 may be attached to the coupling ring 12 enclosing the inner bag liner.

Figure 4:
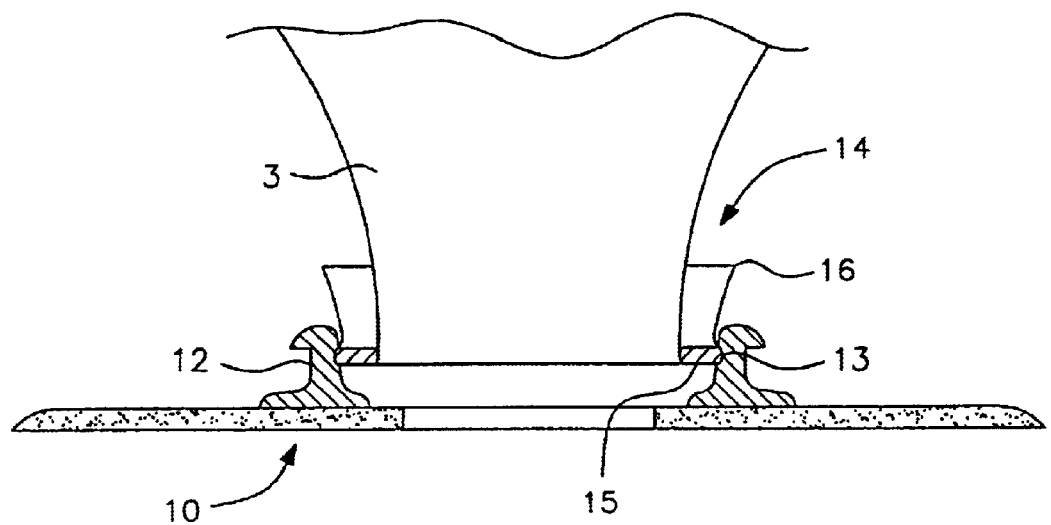
FIG. 4 shows another embodiment of an ostomy appliance inner bag according to the invention with a separate coupling in mesh with a coupling ring attached to a base plate.

Reference is made to FIG. 4 showing another embodiment of an ostomy appliance inner bag according to the invention in mesh with a conventional coupling ring 12 for attaching a conventional collecting bag (not shown). Only the upper inlet end 3 having a general trapezoid shape is shown. The bag 14 is folded over a separate inner bag coupling ring 15 with the free end 16 outside the bag and the inner bag coupling ring 15 is shown in mesh with a groove 13 at the inner side of the coupling ring 12 of the base plate 10. As appears, the inner bag liner is squeezed sealingly between the inner bag coupling ring 15 and the coupling ring 12.

Figure 5:
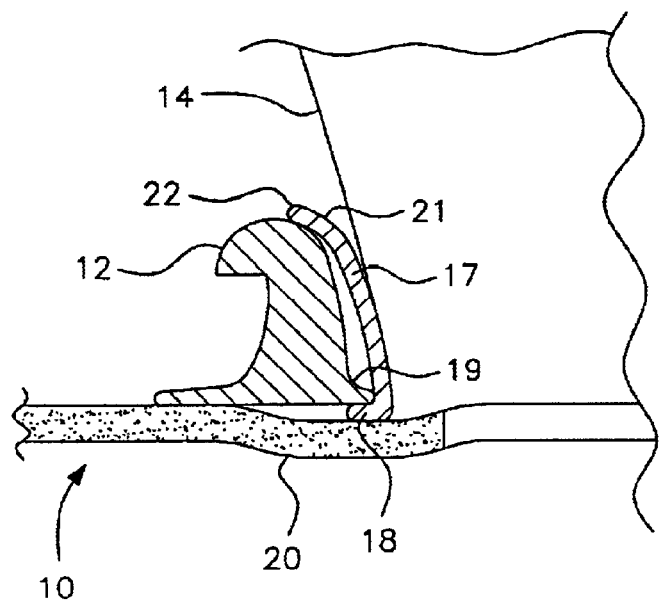
FIG. 5 shows a further embodiment of an ostomy inner bag with a separate coupling ring in mesh with a separate coupling ring attached to a base plate.

FIG. 5 shows a detail of a further embodiment of an ostomy inner bag 14 according to the invention having a separate coupling ring 17 having an outwardly extending rib 18 for engaging with the lower, inner edge 19 of the coupling ring 12. In this embodiment, the attachment of the coupling ring 12 to the adhesive wafer or plate 20 of the base plate 10 is located radially shifted outwards from the inner edge 19 of the coupling ring 12 allowing access to the proximal surface of the coupling ring 12. In FIG. 5 is shown a further preferred detail, viz. an upwardly and outwardly protruding member 21 having an upper end 22 adapted to fit to the upper rim of the coupling ring for preventing the inner bag locking ring from being pushed in too deep when mounted.

Figure 6:
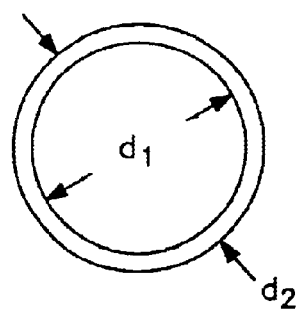
FIGS. 6–8 show preferred dimensioning dimensions.
Figure 7:
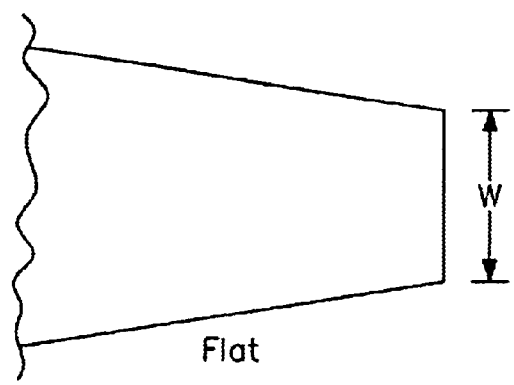
Figure 8:
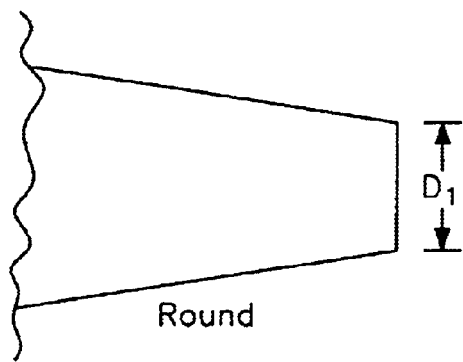

It is believed that in the embodiments of an inner bag shown in FIGS. 4 and 5, certain dimensional proportions are preferred in order to facilitate the use of the bag. The following dimensions are considered as indicated in FIGS. 6–8, FIG. 6 showing a separate inner bag coupling ring having an inner diameter $d_1$ and an outer diameter $d_2$, FIG. 7 showing a flattened inner bag liner having an open end having a width W, and FIG. 8 showing the inner bag liner in open state with an essentially circular opening having diameter $D_1$. The bag is widening to a diameter of at least the inner diameter $d_1$ of the inner bag coupling ring. In order to lock the bag securely it is preferred that $D1<d_2$ is fulfilled. When $W>d_2$ is fulfilled, the bag may easily be drawn through the ring when tilted and folded back and the locking is effected by raising the ring to a position perpendicular to the centre line of the inner bag liner and pushing it outwards until reaching the point where the diameter of the bag is less than $d_2$.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An ostomy appliance comprising:
    an adhesive barrier member having a hole for receiving a stoma, ureter, or catheter, and a barrier wafer to be attached to the wearer's abdomen, back, or chest;
    an outer receiving member having a hole for receiving wastes exiting the stoma, ureter or catheter;
    a disposable inner bag having a hole for receiving wastes exiting the stoma, ureter or catheter, said inner bag fitting within said outer receiving member;
    an inner bag coupling ring separate from said inner bag so as to be separately exchangeable; and
    a single base coupling ring attached to said barrier member and surrounding said barrier member hole, said single base coupling ring having a first coupling area on an inner surface thereof relative to said hole and a second coupling area on an outer surface thereof, said inner bag and inner bag coupling ring being releasably coupled to said barrier member at said first coupling area and said outer receiving member being releasably coupled to said barrier member at said second coupling area.

2. An ostomy appliance as claimed in claim 1 wherein said inner bag coupling ring and said single base coupling ring are concentric.

3. An ostomy appliance as claimed in claim 1 wherein the first coupling area is in the form of a groove in the inner surface of the base coupling ring.

4. An ostomy appliance as claimed in claim 1 wherein the first coupling area is in the form of a recess at a lower inner edge of the base coupling ring.

5. An ostomy appliance as claimed in claim 4 wherein said inner bag coupling ring has an outwardly extending rib for engaging with said recess on the lower inner edge of said base coupling ring.

6. An ostomy appliance as claimed in claim 5 wherein said inner bag coupling ring further includes an upwardly and outwardly protruding member for engaging an upper rim of said base coupling ring to prevent the inner bag coupling ring from being pushed in too far when mounted to said barrier member.

7. An ostomy appliance as claimed in claim 1 wherein the exchangeable inner bag coupling ring has an inner diameter $d_1$ and an outer diameter $d_2$ and the inner bag when flattened has an open end having a width W, said inner bag when in an open state having a generally circular opening with a diameter Dl, said diameter Dl being less than said outer diameter $d_2$.

8. An ostomy appliance as claimed in claim 7 wherein the width W is greater than said outer diameter $d_2$.

9. An ostomy appliance comprising:
    a barrier member having a hole for receiving a stoma, ureter, or catheter;
    an outer receiving member having a hole for receiving wastes exiting the stoma, ureter or catheter;
    a disposable inner bag having a hole for receiving wastes exiting the stoma, ureter or catheter;
    an inner bag coupling ring for coupling said inner bag to said barrier member, said inner bag coupling ring being separate from said inner bag so as to be separately exchangeable; and
    a single base coupling ring attached to said barrier member and surrounding said barrier member hole, said single base coupling ring having a first coupling area on an inner surface thereof relative to said hole and a second coupling area on an outer surface thereof, said inner bag coupling ring being releasably coupled to said barrier member at said first coupling area and said outer receiving member being releasably coupled to said barrier member at said second coupling area, an outer diameter of said inner bag coupling ring being smaller than an inner diameter of said base coupling ring.

10. An ostomy appliance as claimed in claim 9 wherein said inner bag coupling ring and said single base coupling ring are concentric.

11. An ostomy appliance as claimed in claim 9 wherein the first coupling area is in the form of a groove in the inner surface of the base coupling ring.

12. An ostomy appliance as claimed in claim 9 wherein the first coupling area is in the form of a recess at a lower inner edge of the base coupling ring.

13. An ostomy appliance as claimed in claim 12 wherein said inner bag coupling ring has an outwardly extending rib for engaging with said recess on the lower inner edge of said base coupling ring.

14. An ostomy appliance as claimed in claim 13 wherein said inner bag coupling ring further includes an upwardly and outwardly protruding member for engaging an upper rim of said base coupling ring to prevent the inner bag coupling ring from being pushed in too far when mounted to said barrier member.

15. An ostomy appliance as claimed in claim 9 wherein the exchangeable inner bag coupling ring has an inner diameter $d_1$ and an outer diameter $d_2$ and the inner bag when flattened has an open end having a width W, said inner bag when in an open state having a generally circular opening with a diameter Dl, said diameter Dl being less than said outer diameter $d_2$.

16. An ostomy appliance as claimed in claim 15 wherein the width W is greater than said outer diameter $d_2$.

* * * * *